(12) United States Patent
Coleman et al.

(10) Patent No.: US 6,264,666 B1
(45) Date of Patent: Jul. 24, 2001

(54) WATER JET FOR DERMATOLOGICAL TREATMENT

(76) Inventors: William P. Coleman, 10 Tara Pl., Metaire, LA (US) 70002; Ren-Yeu Tsai, 199 Tung Hwa North Rd., Taipei (TW)

(*) Notice: Subject to any disclaimer, the term of this patent is extended or adjusted under 35 U.S.C. 154(b) by 0 days.

(21) Appl. No.: 09/013,714

(22) Filed: Jan. 26, 1998

(51) Int. Cl.[7] .................................................. A61B 17/50
(52) U.S. Cl. ........................... 606/131; 606/2; 606/9; 606/201; 606/132; 606/134; 606/204.35; 604/257; 433/84; 433/88; 433/89
(58) Field of Search ................................. 606/9, 131, 2, 606/201, 204.35, 132, 134, 156, 158, 159; 604/257; 433/84, 88, 89

(56) References Cited

U.S. PATENT DOCUMENTS

| | | |
|---|---|---|
| Re. 31,887 | 5/1985 | Hodgson . |
| 4,183,470 | 1/1980 | Hovartos et al. . |
| 5,186,625 * | 2/1993 | Bailey ................................... 433/88 |
| 5,240,842 | 8/1993 | Mets . |
| 5,350,299 * | 9/1994 | Gallant ................................... 433/88 |
| 5,362,494 | 11/1994 | Zysmann et al. . |
| 5,441,174 | 8/1995 | Sperry . |
| 5,547,376 * | 8/1996 | Harrel ................................... 433/116 |
| 5,591,184 * | 1/1997 | McDonnell et al. ................. 606/167 |
| 5,634,791 * | 6/1997 | Matsuura et al. ...................... 433/87 |
| 5,657,760 | 8/1997 | Ying et al. . |
| 5,752,829 * | 5/1998 | Goldsmith et al. .................... 433/88 |

\* cited by examiner

Primary Examiner—Michael Buiz
Assistant Examiner—(Jackie) Tan-Uyen Ho

(57) ABSTRACT

A system for the removal of epidermal and dermal skin through the use of a pressurized stream of water. The surgeon chooses the pressure of the water to obtain the desired abrasive affect. In one embodiment of the invention, a benign abrasive is added to the water to assist in the removal of the surface cells of the skin. In other embodiments, a variety of medications are added to the water such as: anesthetics to deaden the skin being abraded; coagulants to minimized bleeding in the abraded area; and antiseptics to combat infection after treatment is applied. In one embodiment of the invention, a catch reservoir is positioned around the site being treated to collect and withdraw the spent liquid and removed cells.

14 Claims, 10 Drawing Sheets

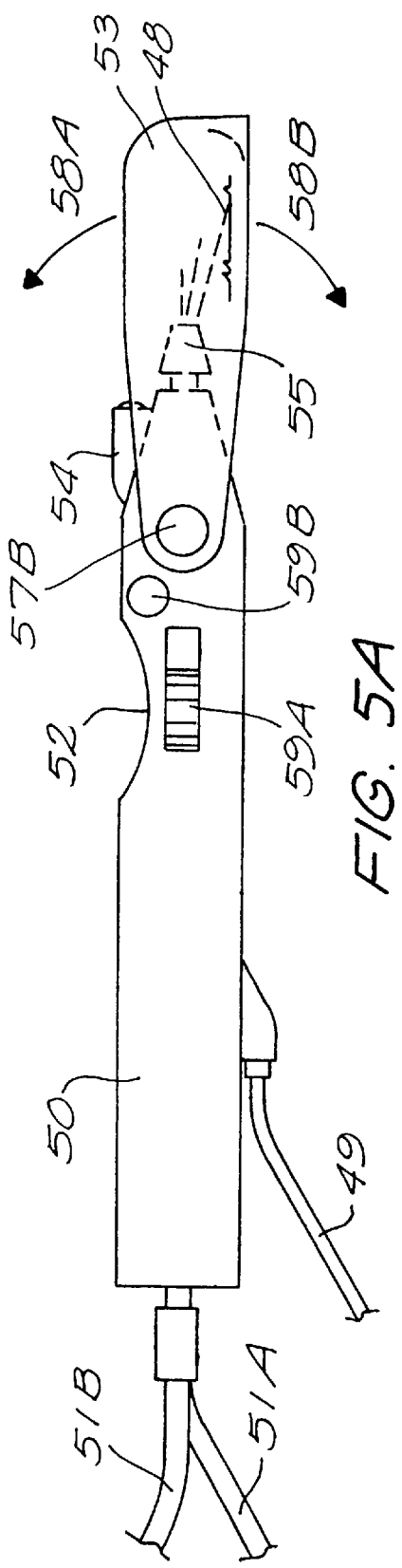
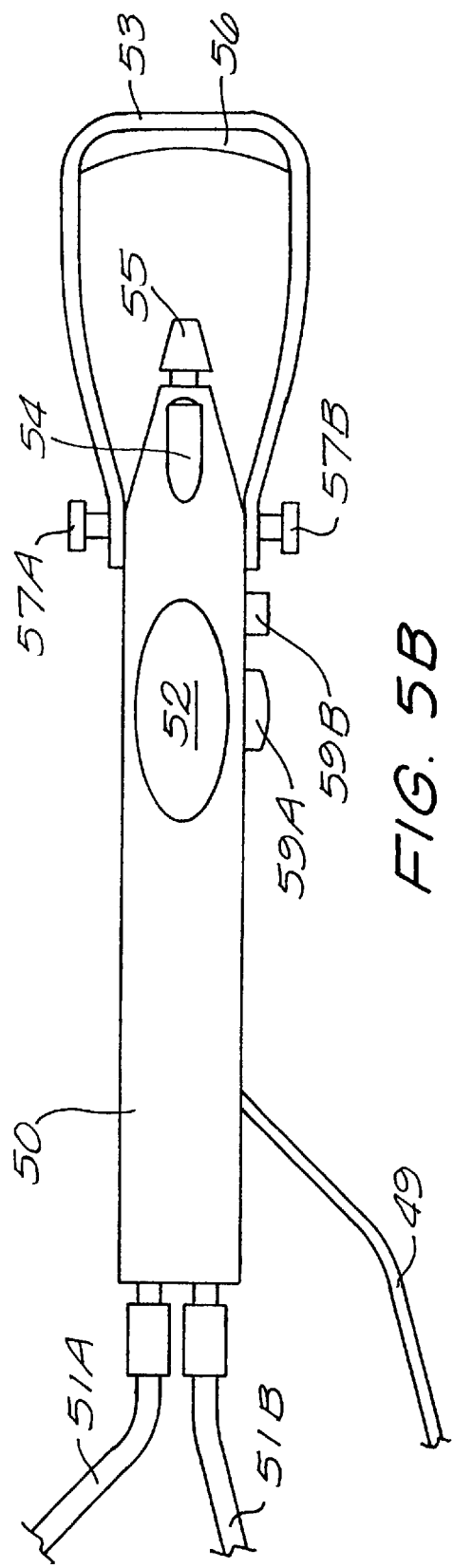
FIG. 5A
FIG. 5B

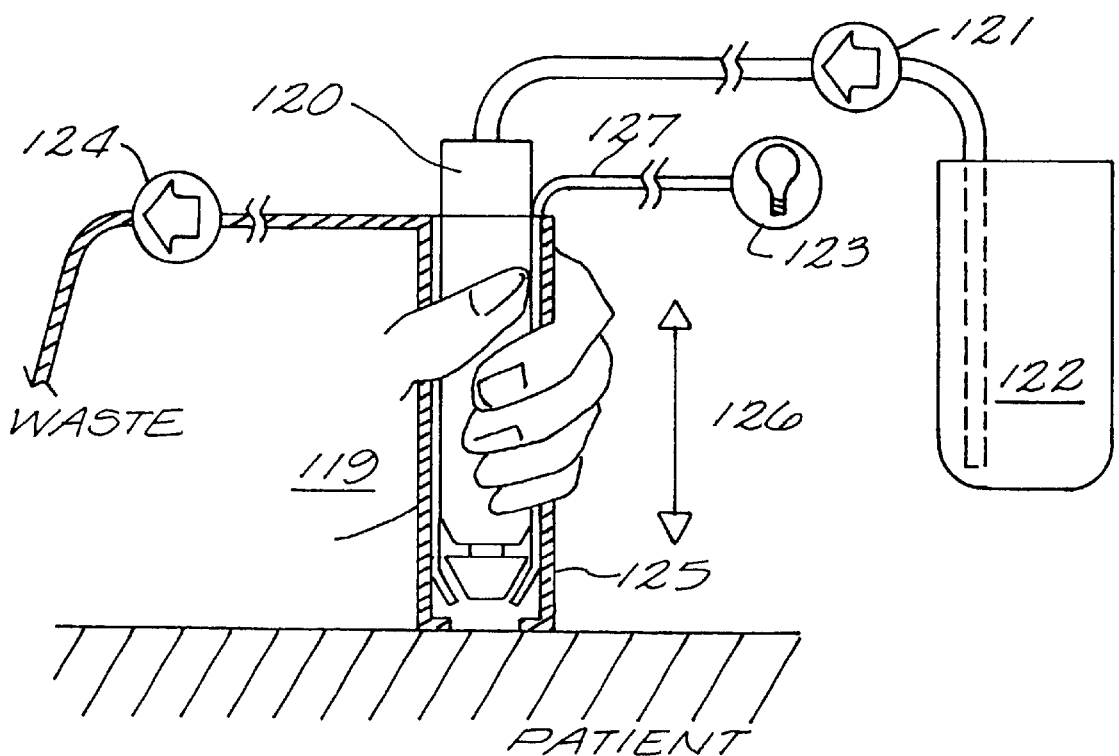
FIG. 12A
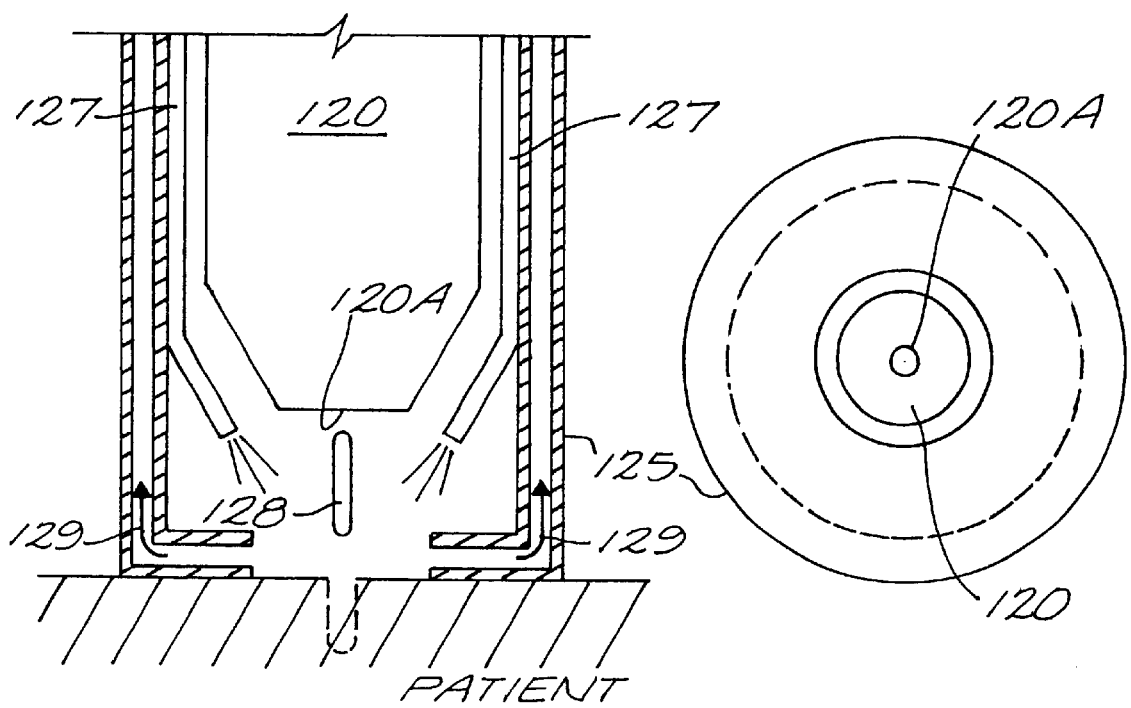
FIG. 12B
FIG. 12C

WATER JET FOR DERMATOLOGICAL TREATMENT

BACKGROUND OF THE INVENTION

This invention relates generally to cosmetic surgery and more particularly to treatment of dermatological conditions.

Within cosmetic surgery, dermatological treatments remain one of the largest problems. The current modalities available for skin resurfacing include chemical peeling, dermabrasion, and laser resurfacing.

Chemical peeling involves the application of a variety of chemicals to the skin with the intent of producing a chemical burn of a predictable depth. Depending on the agent applied, the skin responds as a chemical burn. Necrotic tissue peels off and is scavenged by macrophages eventually leading to a healing wound. Depending on the depth of the wound new collagen fibers are produced resulting in a thicker more elastic (youthful) appearing skin. At the same time, surface irregularities such as pigmentation problems or textural problems are removed by the peeling and new smoother skin of a more even color replaces it.

Dermabrasion involves removing layers of skin through an abrasive process. Either a diamond fraise or a wire brush is attached to a motor driven rotating device which allows the operator to "sand" down the skin to a given depth. This is different than chemical peeling in that an abrasive wound begins to heal immediately after the injury. There is no delay in wound healing for tissue to peel off or for macrophage to clean up necrotic cells. Abraded wounds depending on the depth also result in improved texture and skin color as well as the deposition of new collagen fibers for thicker more youthful skin. Motorized dermabrasion has also been used for almost a century for smoothing facial scars.

Laser resurfacing is the newest skin resurfacing modality. Currently, ultra pulsed lasers are used to vaporize skin. This extremely precise process burns away tissue to a specific depth. Thermal damage to the remaining tissue is kept at a minimum because the laser pulses at an extremely rapid rate. Similar to dermabrasion, the skin is removed at the time of surgery but some necrotic tissue is left behind which must be scavenged by macrophage before wound healing can ensue. Laser resurfacing also results in even color and texture to skin as well as the deposition of new collagen fibers.

The three current modalities for skin resurfacing are able to be used interchangeably. Each has its own specific advantages according to the pathology involved and the location of the skin being treated.

None of these modalities provides the ideal method of skin resurfacing. Dermabrasion comes most close to the ideal in that wound healing is able to begin immediately after the surgery. Thus the potential for infection from bacteria and viruses is reduced over chemical peeling and especially laser resurfacing. However, dermabrasion results in brisk bleeding during surgery. This has been suggested to present a danger to both the surgeon and assistants. In aerolized form, the bleeding can also contaminate other individuals in the vicinity of the ventilation system. Also patients are unhappy with the appearance of abrasive wounds and are naturally fearful of bleeding surgical sites.

It is clear from the foregoing that there is a need for an efficient and safe mechanism for the treatment of dermatological conditions.

SUMMARY OF THE INVENTION

The present invention creates a system for the removal of epidermal and dermal skin through the use of a pressurized stream of water. Water, or another stream of liquid, is directed against the skin layer to abrade the surface cells of the epidermis.

The abrasion process involves repeatedly passing the stream of pressurized water against a site to selectively remove successive cell layers until the proper effect is obtained.

In this task, the surgeon chooses the pressure of the water to obtain the desired abrasive affect. The key is to obtain the desired water pressure that removes the layer without cutting the skin too deeply. In this context, a pressure of fifty pounds per square inch is desired although other pressures are also useable.

The pressure chosen must also be tempered with the width of the water spray being used. A wider diameter spray, even at a high pressure is less likely to cut than a thinner spray. In the preferred embodiment, the tip of the probe is equipped with replaceable nozzles which direct the spray in varying bands and which can be adjusted by the surgeon to have a particular orientation (from horizontal to a vertical orientation).

In this context, a water jet dissector is modifiable for skin abrasion.

In another embodiment of the invention, a benign abrasive is added to the water to assist in the removal of the surface cells of the skin. This abrasive is chosen so that any fragments which may remain embedded in the skin after the treatment, do not have any adverse affects upon the patient and are naturally removed by the patient's own immune system.

Some such abrasive include rock salt, ice, and hardened starch. Often such abrasives react with water and are softened by prolonged exposure to the water. In this case, the abrasive is applied to the water as proximate in time to use of the abrasive as possible to keep the abrasive from losing its ability to abrade the skin.

In other embodiments, a variety of medications are added to the water such as: anesthetics to anesthetisize the skin being abraded; coagulants to minimize bleeding in the abraded area; and antiseptics to combat infection after treatment has been applied.

Those of ordinary skill in the art readily recognize a variety of medications which serve the above functions and other medications which can be used in this context.

Note that the medications are forced into the epidermis due to the water pressure applied during application and as such form a layer of medicated skin after the surgical procedure has been completed.

While in most applications the waste water and debris the procedure generates is removed using a catch reservoir positioned around the site being treated to collect and withdraw the spent liquid and removed cells.

The preferred catch reservoir is a generally circular shaped mechanism which is placed around the surgical site and is then connected to a vacuum pump. The vacuum pump draws air through a channel within the catch reservoir with strategically placed portals so that the waste water and debris is pulled away from the surgical site for appropriate disposal.

This attribute assists in keeping the surgical site clear of water so that the pressurized spray from the surgeon has optimal effectiveness and also assures a clear site for viewing by the surgeon.

In the preferred embodiment, the apparatus is a water driven device with various sized skin probes. The probe both delivers water at high speeds and at the same time suctions away debris and contaminated water. In this manner, the device removes the epidermis and upper dermis. The depth of skin removal is controlled by the rate of water delivery.

Through the use of various sized probes, local skin removal or large areas of skin removal is easily and effectively accomplished.

Water resurfacing is highly advantageous since a clean wound is created while at the same time avoiding the potential for blood splatter and contamination is significantly reduced. The clean wound created by the water resurfacing is much less prone to bacterial and viral infections and more rapidly heals than any of the other resurfacing modalities.

The invention, together with various embodiments thereof, will explained in more detail by the accompanying drawings and following description.

DRAWINGS IN BRIEF

FIGS. 5A and 5B are side and top views of the preferred embodiment of the probe.

DRAWINGS IN DETAIL

Figure 1:
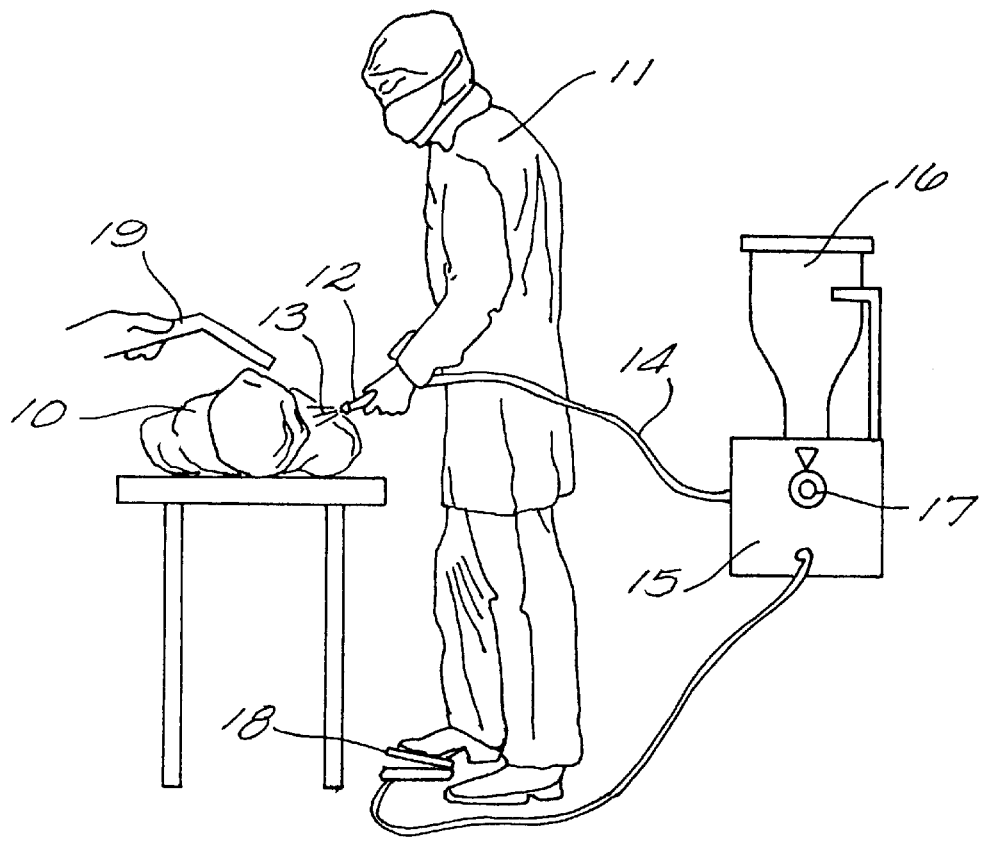
FIG. 1 is a side view of an embodiment of the invention being used by a surgeon.

FIG. 1 is a side view of an embodiment of the invention being used by a surgeon.

Surgeon 11 directs probe 12 to the area for the abrasion of epidermal cells on patient 10. A stream of pressurized water 13 is emitted from probe 12 to impact on the site. Successive movement across the site dislodges successive layers of epidermal and dermal cells. In this embodiment, suction tube 19 is manipulated to withdraw spent water and debris from the site.

Pressurized water is provided to probe 12 via hose 14 which is connected to pump 15. Water is withdrawn from reservoir 16 for use in this process. The level of pressurization of stream 13 is established via control knob 17.

When surgeon 11 depresses foot switch 18, water is directed from pump 15 to probe 13 for use thereby.

As noted before, within this context sterile water is the preferred liquid although other suitable liquids are also obvious to those of ordinary skill in the art including alcohol or a combination of alcohol and water.

Figure 2:
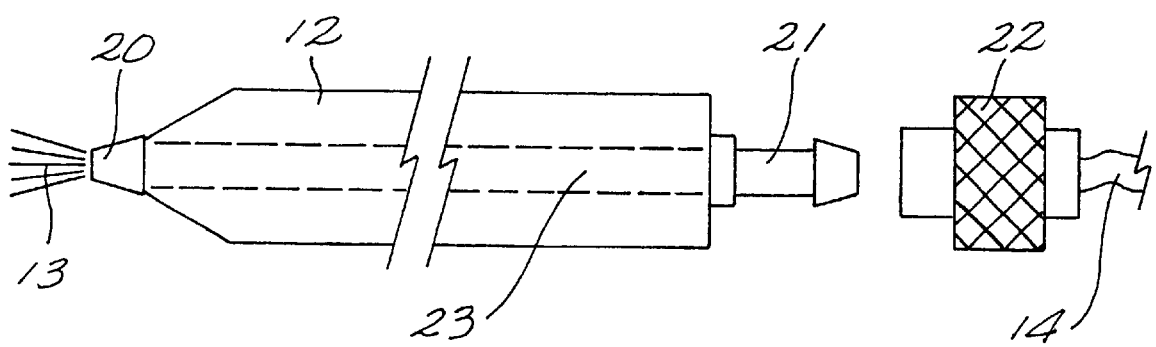
FIG. 2 is a side view of an embodiment of the probe used for the water abrasion of epidermal cells.

FIG. 2 is a side view of an embodiment of the probe used for the water abrasion of epidermal cells.

Probe 12, first illustrate Through proper selection of nozzle 20, characteristics of spray 13 are readily alterable to accomplish the task chosen by the surgeon.

Probe 12 is connected to hose 14 via male connector 21 which slips into and is secured to slide connector 22. In this manner, a variety of probes are easily interchanged and connected to hose 14 for selected uses by the surgeon.

Figure 3:
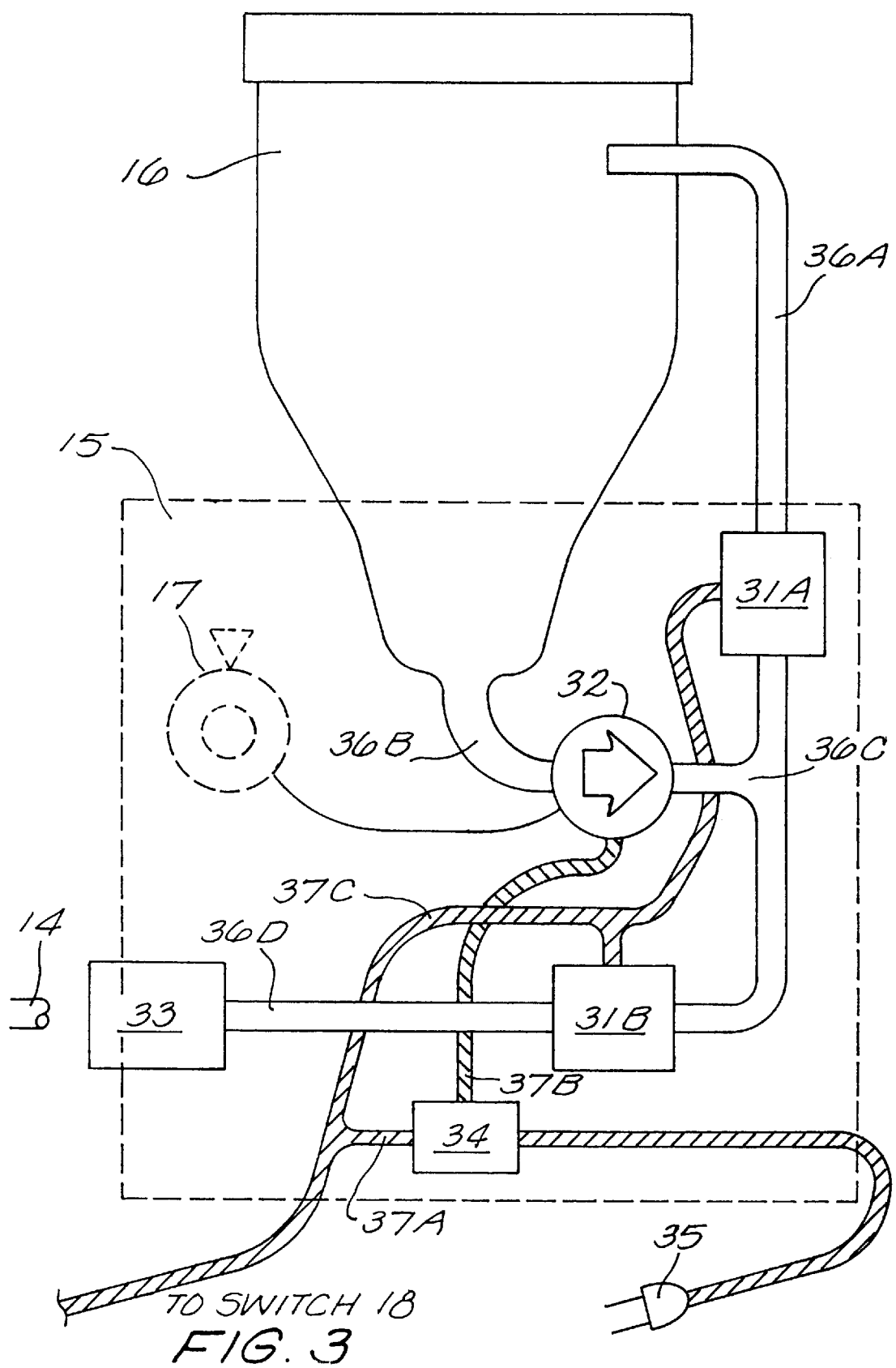
FIG. 3 is a side view of the pump illustrated in FIG. 1 showing the plumbing and electrical connections.

FIG. 3 is a side view of the pump illustrated in FIG. 1 showing the plumbing and electrical connections.

As noted with relation to FIG. 1, reservoir 16 holds the sterile water which is to be used in this application. Water from reservoir 16 is communicated by pipe 36B to pump 32 which provides a cter from pump 32 is discharged into pipe 36C.

When water is not being used in the abrading function, valve 31A is open and valve 31B is closed; hence, the pressurized water within pipe 36C is communicated via pipe 36A back into reservoir 16.

When water is being used for abrasion, valve 31B is open and valve 31A is closed; pressurized water is then passed from pipe 36C through valve 31B into pipe 36D for communication through connector 33 to hose 14 which communicates with the probe (not shown in this illustration).

Electrical energy is used to control valves 31A and 31B. Electrical energy is obtain via plug 35 which communicates electrical energy to electrical connector 34. At electrical connector 34, electrical energy is directed to flow to pump 32 via wire 37B and to foot switch 18 via wire 37A.

The foot switch, when activated, communicates the electrical energy back to valves 31A and 31B via wire 37C. In a passive condition, valve 31A is open and valve 31B is closed. When electrical energy is applied, valves 31A and 31B change to the opposing state (closed and open respectively).

In this manner, a selected water pressure level is obtained and maintained for the surgeon's use.

Figure 4A:
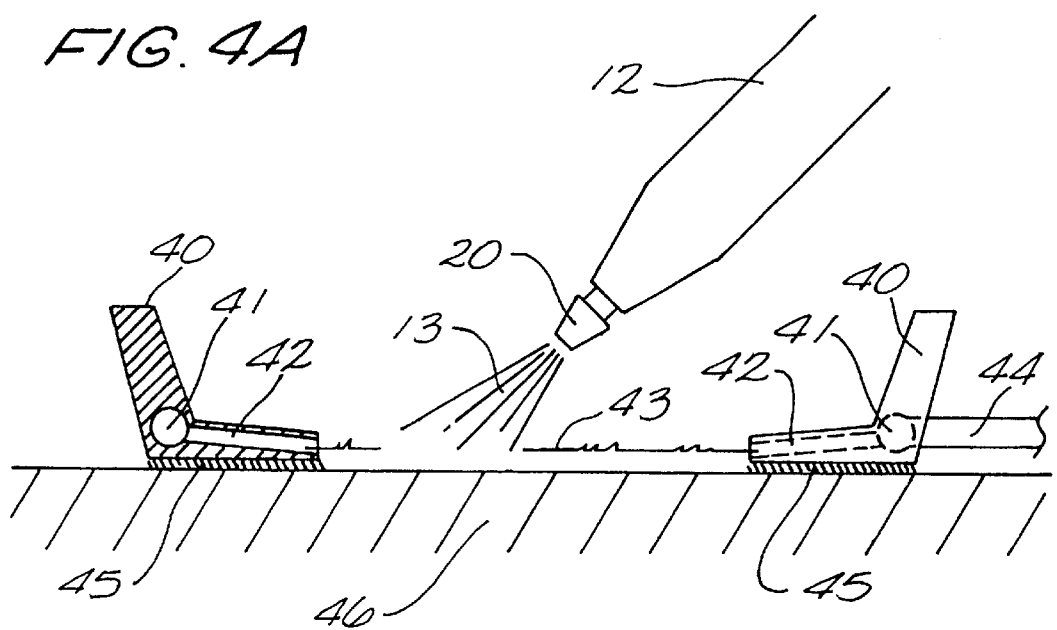
FIGS. 4A and 4B are side and top views of the preferred catch basin.
Figure 4B:
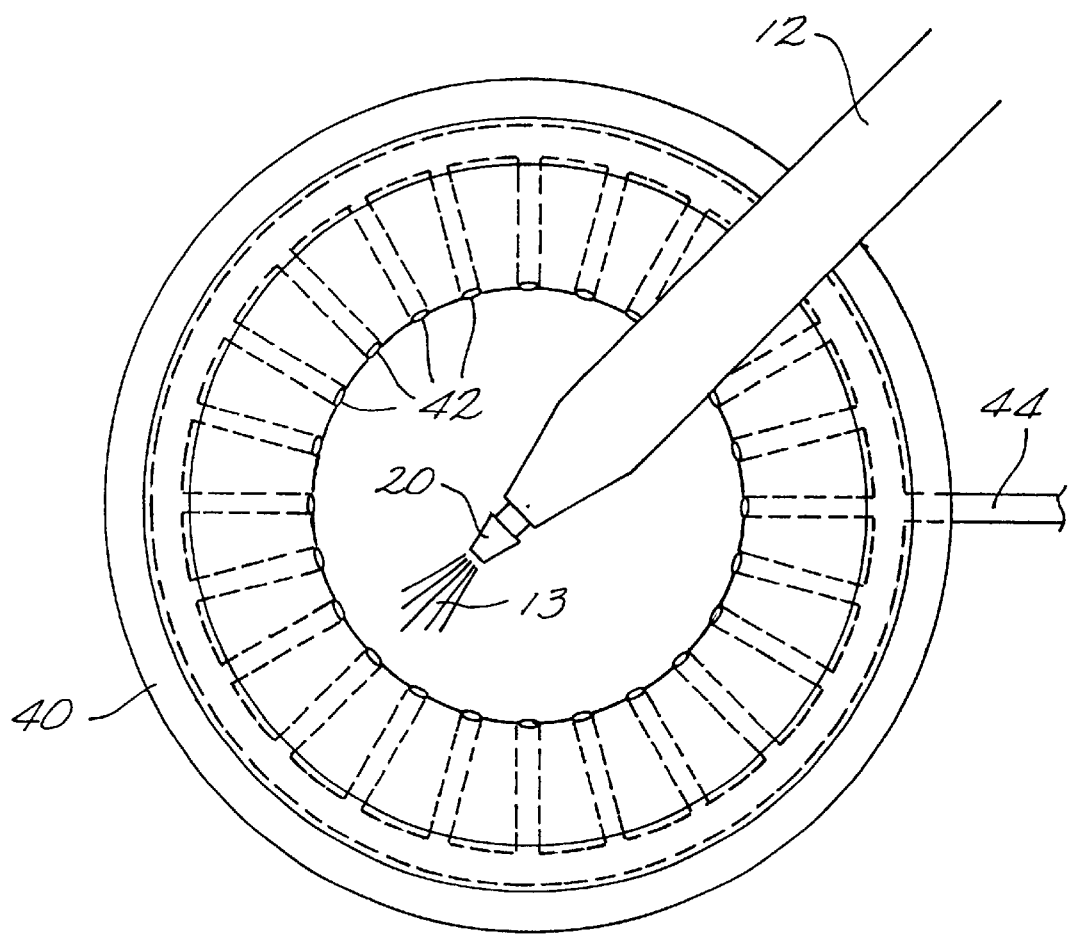

FIGS. 4A and 4B are side and top views of the preferred catch basin.

Referring to both FIGS. 4A and 4B, in this embodiment catch basin 40 is generally circular in shape and is secured to skin 46 of patient via adhesive 45. Since catch basin 40 is open in the center, probe 12 is able to direct pressurized water 13 via nozzle 20 against the epidermis at the surgical site.

An internal channel 42 extends around the circumference of catch basin 40. The internal channel 42 communicates with the interior portion via portal channels 42 which exit proximate to the base of the catch basin. Tube 44 communicates with internal channel 42 and a suction pump (not shown).

The suction pump creates a partial vacuum which draws spent water 43 and debris through channels 42, into internal channel 42 to finally be discarded. In this manner, the surgical site is kept free of spent water and debris providing the surgeon a clear view of the site.

FIGS. 5A and 5B are side and top views of the preferred embodiment of the probe.

Grip 50 includes thumb rest 52. Pressure adjustment switch 59A is positioned to be controlled by the surgeon's fore-finger. In similar manner, on/off switch 59B is also positioned to be activated by the surgeon's fore-finger.

As discussed before, pressurized water is communicated to the probe via hose 51A. The pressurized water is communicated via an internal channel within the probe to exit via nozzle 55.

In this embodiment, shield 53 is secured to probe 50 via screws 57A and 57B which allow rotational adjustment of shield 53 as shown by arrows 58A and 58B. This rotation of shield 53 provides a depth control guide. In application, the base of shield 53 is pulled or pushed along the skin; shield 53 maintains nozzle 55 at the chosen distance from the skin. By maintaining nozzle 55 at a set distance from the skin layer, optimal abrasion without excessive damage is obtained.

Shield 53 is further equipped in this embodiment with a catch tray 56 which collects the spent water 48. This spent water is drawn through holes (not shown) near the catch tray to be drawn through hose 51B and then properly discarded.

To assist with the viewing of the site, this embodiment is equipped with lamp 54. Power for lamp 54, as well as communication channels for pressure adjustment switch 59A and on/off switch 59B, is provided by electrical hookup 49 which communicates with the pump (not shown).

Figure 6:
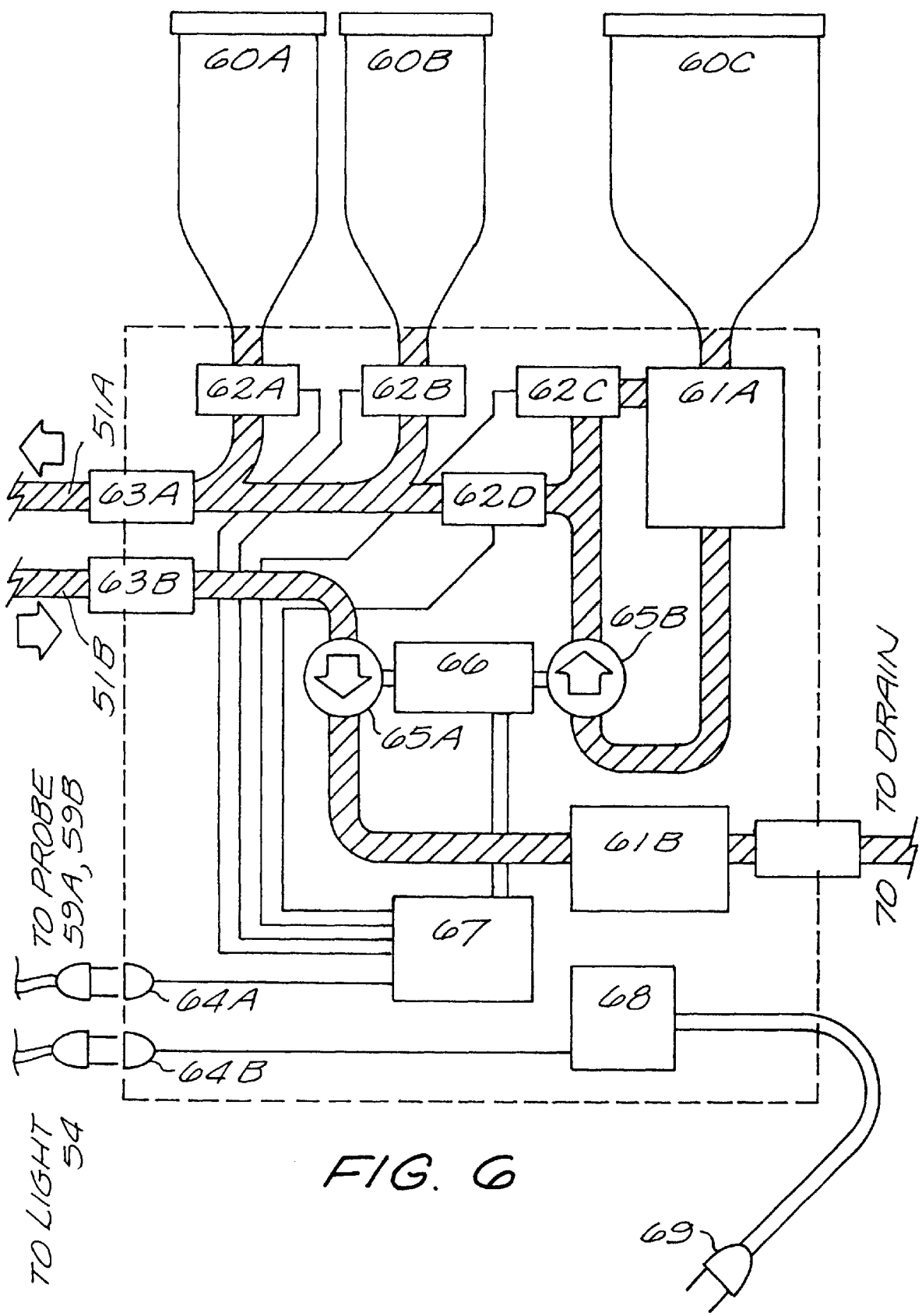
FIG. 6 is a side view of the preferred pump mechanism.

FIG. 6 is a side view of the preferred pump mechanism.

Reservoir 60A is used to contain a benign abrasive; reservoir 60B is used to contain a chosen medicinal component or combination of medicines; and reservoir 60C is used to contain the sterile water.

Water from reservoir 60C is communicated into internal reservoir 61A. In a manner similar to that described in FIG. 3, pump 65B draws water from internal reservoir 61A and provides pressurized water to valves 62C and 62D which are selectively activated by control circuit 67 to either re-circulate the water to internal reservoir 61A or to be communicated via connector 63A to hose 51A for use by the probe described in FIGS. 5A and 5B.

When pressurized water is communicated to the probe via connector 63A, valve 62A is opened to let the benign abrasive enter the channel, and valve 62B is opened to permit the medicine to enter the channel to form a composite stream of water/abrasive/medicine to the probe.

Motor 66 is used to drive pump 65B and pump 65A. Pump 65A is used to suction spent water and debris via hose 51B from the surgical site via connector 63B and to deposit the spent water and debris into internal reservoir 61B. After the surgery, the contents of internal reservoir 61B are dumped into drain 70.

Control circuit 67 is used to operate motor 66 and to activate valves 62A, 62B, 62C, and 62D. Power to control circuit 67 is provided from plug 69 which connects through connector box 68 with control circuit 67 as well as with light 54 via electrical connector 64B.

Surgeon adjustment of the control circuit 67 is provided from switches 59A and 59B (described in FIGS. 5A and 5B) and are communicated via connector 64A.

Figure 7:
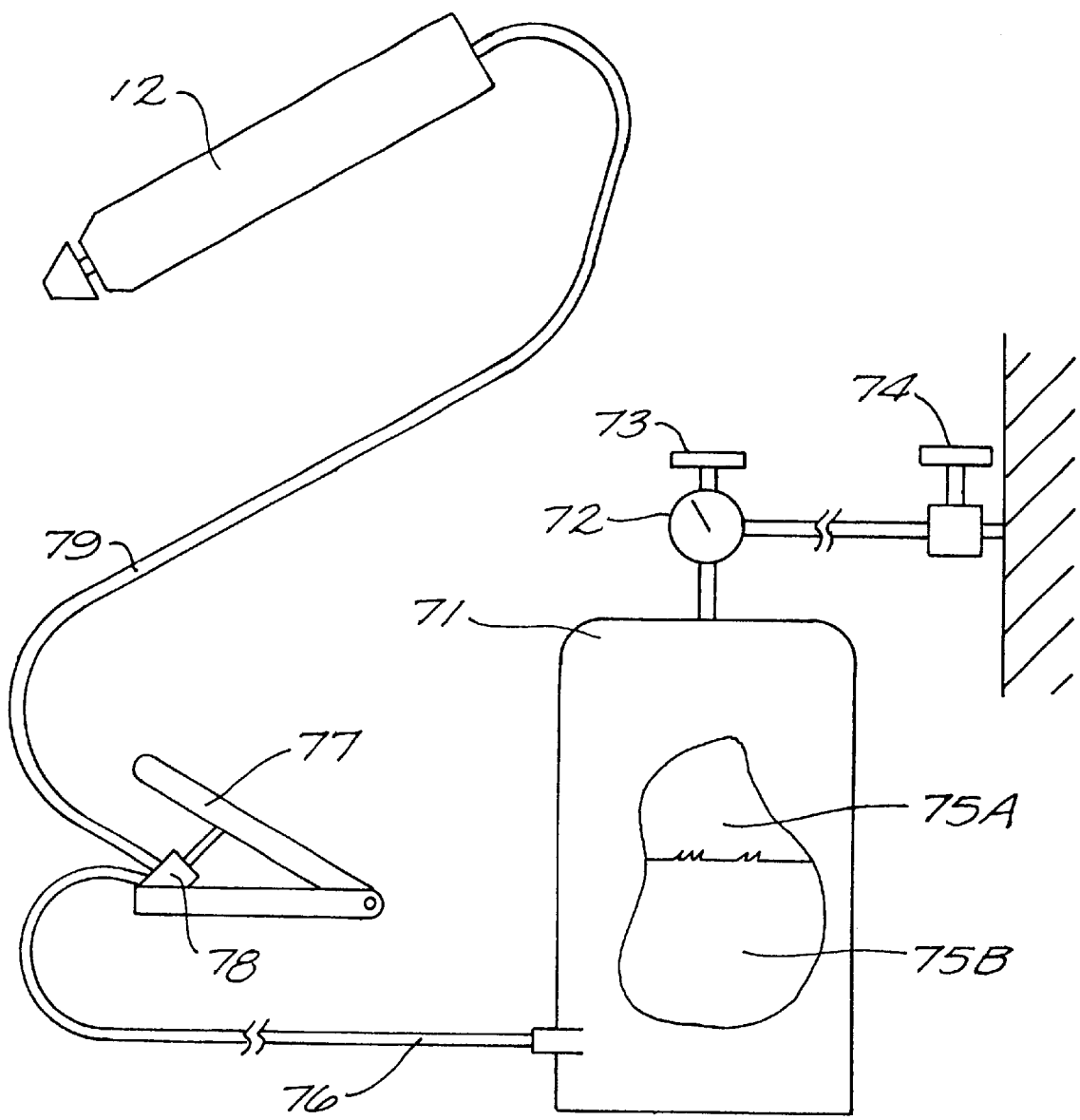
FIG. 7 is a side view of a mechanism used to deliver pressurized water.
Figure 8:
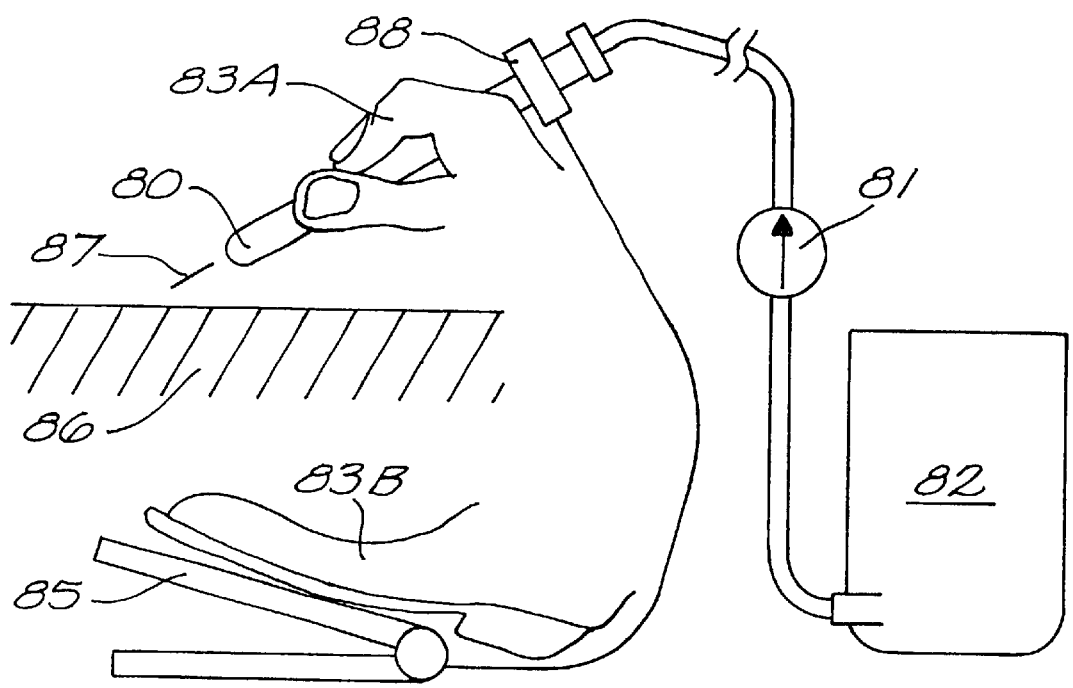
Figure 9A:
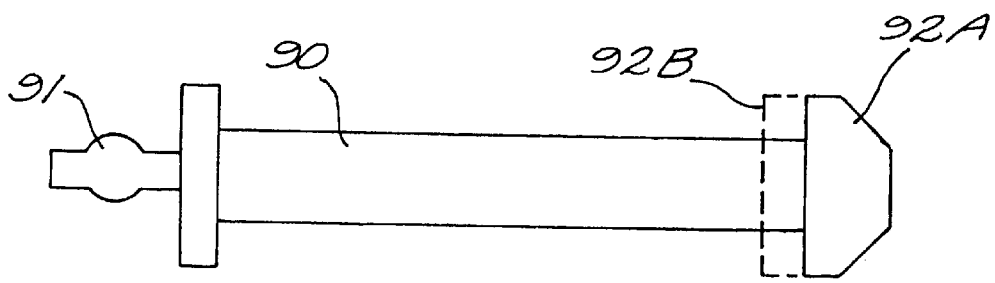
Figure 9B:
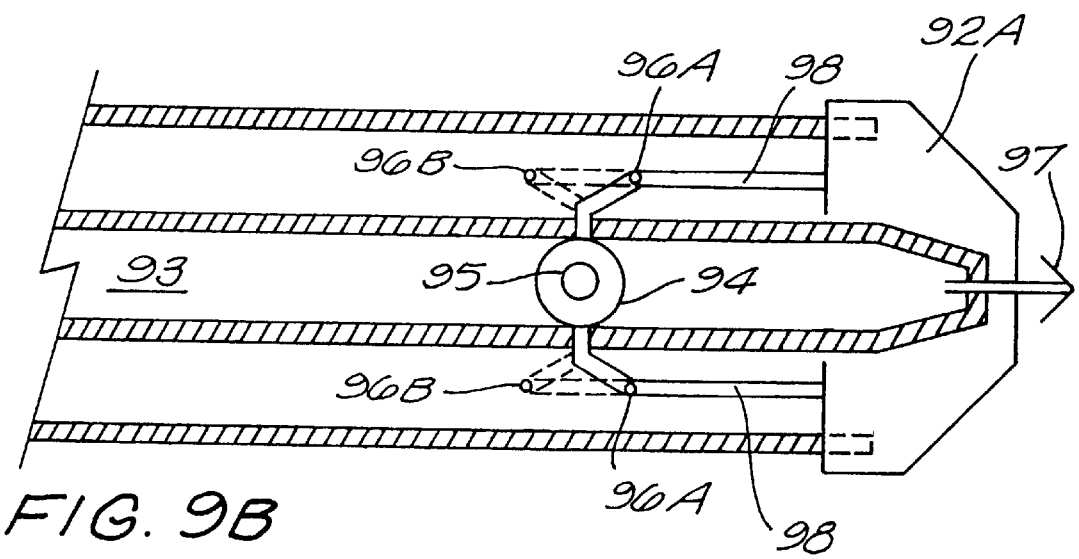
Figure 10A:
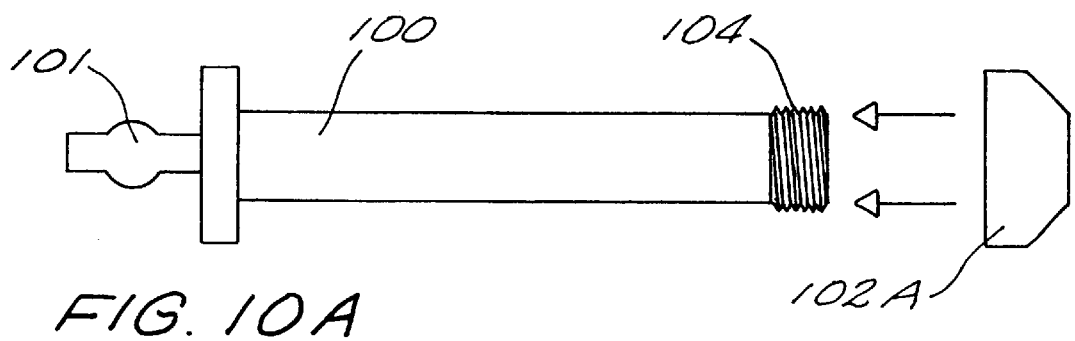
Figures 10B, 10C, 10D:
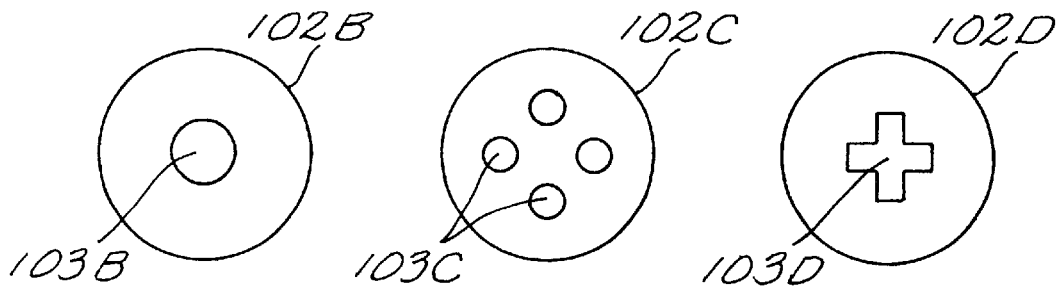
Figure 11:
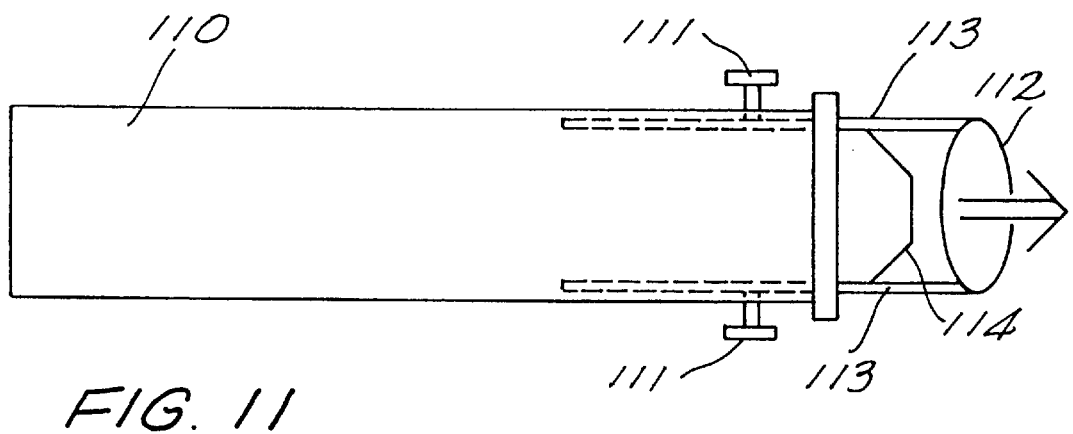
Figure 13:
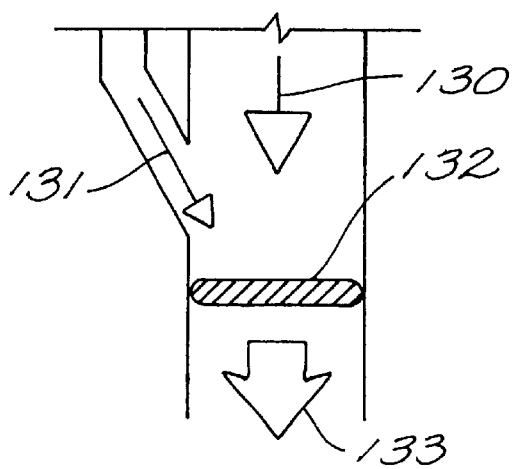
Figure 14:
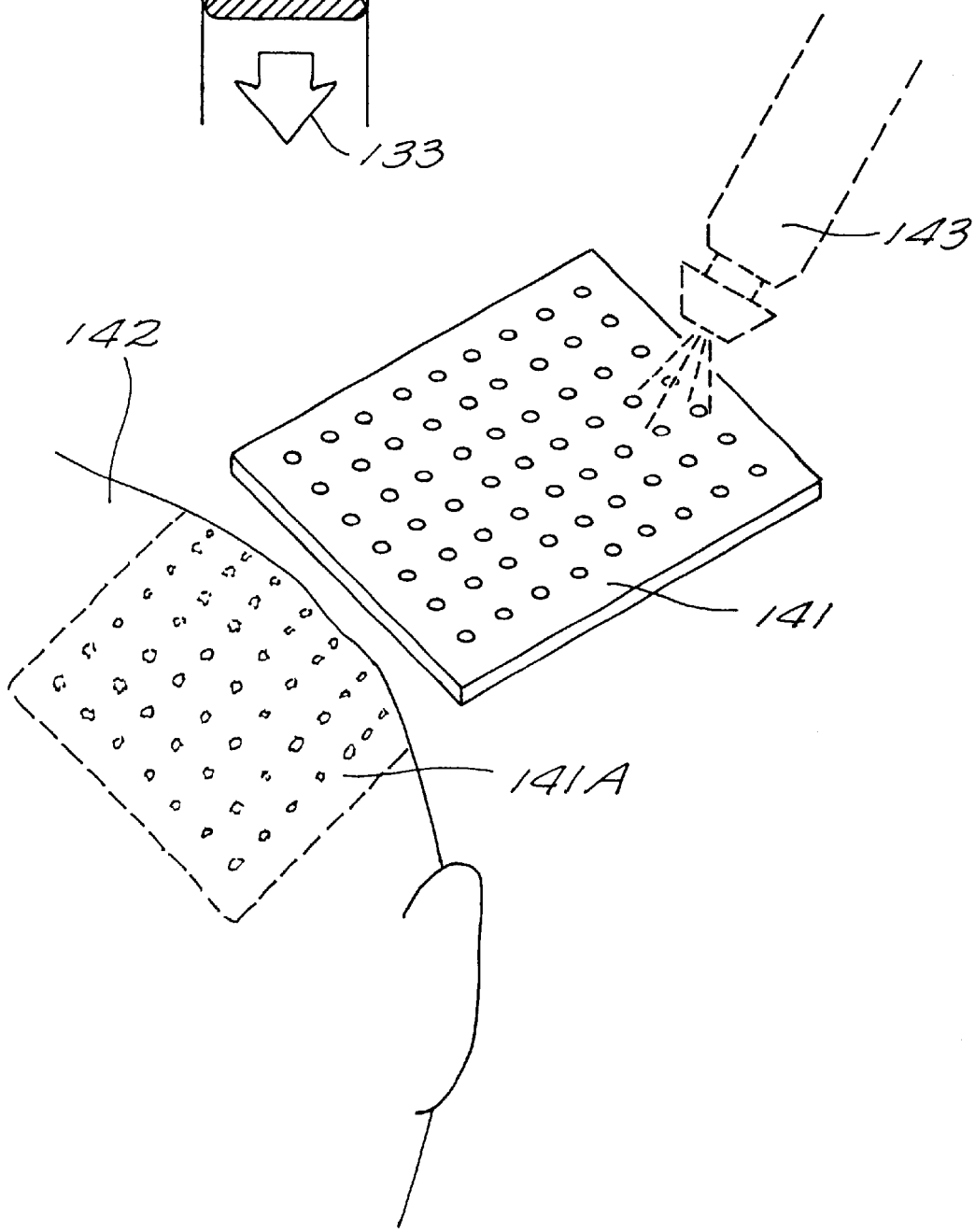

FIG. 7 is a side view of a mechanism used to deliver pressurized water.

Pressure container 71 contains both a volume of sterile water 75B and an air volume 75A. An air pressure source is turned off/on by valve 74 which communicates with adjustment valve 72. The pressure level of air volume 75A is controlled by the surgeon through adjustment of handle 7.

Pressure in air volume 75A is transferred to the water volume 75B which is forced through tubing 76 and is communicated to valve 78. As the surgeon depresses foot lever 77, valve 78 is opened letting the sterile water to pass through tubing 79 to probe 12.

In this manner, the surgeon is able to select the desired pressure and then selectively use the pressurized water for the abrading operation.

It is clear that the present invention creates a highly improved apparatus and technique for the abrading of epidermal cells.

What is claimed is:

1. An apparatus adapted for the selective abrasion of an epidermis of a patient comprising:
    a) a reservoir containing substantially pure water;
    b) a pump connected to said reservoir, said pump generating an operator defined water pressure; and,
    c) a handle member having,
        1) a nozzle,
        2) a light source directed to emit light past said nozzle, and,
        3) a valve adapted to direct water from said pump through said nozzle, said valve being selectively engaged by a surgeon.

2. The apparatus according to claim 1 further including means for applying a selected quantity of medicinal material to said substantially pure water from said nozzle.

3. The apparatus according to claim 1 further including:
    a) a catch reservoir adapted to be positioned around a chosen site of skin and allowing surgeon access therethrough to said site of skin, said catch reservoir having an internal channel, and a plurality of portals extending from said internal channel, said plurality of portals exposed proximate to a lower portion of said catch reservoir; and,
    b) evacuation means connected to said internal channel for withdrawing liquids entering said plurality of portals.

4. The apparatus according to claim 3 wherein said pump and said evacuation means are driven by a common motor.

5. The apparatus according to claim 3 wherein said catch reservoir is adapted to direct liquid to said plurality of portals.

6. The apparatus according to claim 5 further including an adhesive positioned on a first side of said catch reservoir and adapted to secure said catch reservoir to skin of a patient around the site of epidermis.

7. The apparatus according to claim 1 wherein said valve includes a foot activated valve.

8. The apparatus according to claim 1 wherein said valve is positioned on said handheld nozzle.

9. The apparatus according to claim 8 further including:
    a) a debris catcher positioned downstream of said handheld nozzle;
    b) a waste reservoir; and,
    c) evacuation means connected to said debris catcher for drawing liquids collected in said debris catcher to said waste reservoir.

10. The apparatus according to claim 9 further including a guide member connected to said handheld nozzle and adapted to maintain the leading end said handheld nozzle a selected distance from the skin.

11. An epidermal and dermal skin removal system adapted for the selective abrasion of an epidermis and dermal of a patient comprising:
    a) a source of a sterile liquid lacking a suspended abrasive conveyed under selected pressure;
    b) a handheld nozzle; and,
    c) an operator manipulatable valve adapted to direct sterile liquid from said source to said handheld nozzle, said sterile liquid having sufficient pressure that when directed against said epidermis and dermal of said patient, cells from said epidermis and dermal are readily abraded.

12. The epidermal and dermal skin removal system according to claim 11 further including:
   a) a catch reservoir adapted to be positioned around a chosen site of epidermis said catch reservoir adapted to direct liquids away from the site of epidermis; and,
   b) evacuation means for drawing liquids from said catch reservoir.

13. The epidermal and dermal skin removal system according to claim 11 further including:
   a) a debris catcher positioned in front of said handheld nozzle;
   b) a waste reservoir; and,
   c) evacuation means connected to said debris catcher for drawing liquids collected in said debris catcher to said waste reservoir.

14. The epidermal and dermal skin removal system according to claim 13 further including a light source connected to said handheld nozzle and adapted to direct a beam of light past the leading end of said handheld nozzle.

* * * * *